(12) United States Patent
Stettner et al.

(10) Patent No.: US 12,115,346 B2
(45) Date of Patent: Oct. 15, 2024

(54) INFUSION ARRANGEMENT FOR ADMINISTERING A MEDICAL FLUID

(71) Applicant: B. Braun Melsungen AG, Melsungen (DE)

(72) Inventors: Jens Stettner, Melsungen (DE); Jens Wildhagen, Hannover (DE)

(73) Assignee: B. Braun Melsungen AG, Melsungen (DE)

(*) Notice: Subject to any disclaimer, the term of this patent is extended or adjusted under 35 U.S.C. 154(b) by 790 days.

(21) Appl. No.: 17/295,939

(22) PCT Filed: Oct. 24, 2019

(86) PCT No.: PCT/EP2019/079107
§ 371 (c)(1),
(2) Date: May 21, 2021

(87) PCT Pub. No.: WO2020/114677
PCT Pub. Date: Jun. 11, 2020

(65) Prior Publication Data
US 2021/0393874 A1    Dec. 23, 2021

(30) Foreign Application Priority Data
Dec. 4, 2018  (DE) .................. 10 2018 220 890.5

(51) Int. Cl.
*A61M 5/152*    (2006.01)
*A61M 5/168*    (2006.01)

(52) U.S. Cl.
CPC ........ *A61M 5/152* (2013.01); *A61M 5/16813* (2013.01); *A61M 5/16881* (2013.01);
(Continued)

(58) Field of Classification Search
CPC ...... A61M 5/152; A61M 5/155; A61M 5/142; A61M 5/14; A61M 5/148; A61M 5/1483;
(Continued)

(56) References Cited

U.S. PATENT DOCUMENTS 2,527,814 A  * 10/1950  Hanssen ............. F16K 31/1264
                                                    92/100
3,468,308 A     9/1969  Bierman
(Continued)

FOREIGN PATENT DOCUMENTS

CA       1243251 A      10/1988
CN     101025236 A       8/2007
(Continued)

OTHER PUBLICATIONS

Search Report received in German Application No. 10 2018 220 890.5 dated Oct. 23, 2019, with translation, 18 pages.
Search Report received in International Application No. PCT/EP2019/079107 dated Feb. 12, 2020, with translation, 5 pages.
(Continued)

*Primary Examiner* — Courtney B Fredrickson
*Assistant Examiner* — Macy C Frank
(74) *Attorney, Agent, or Firm* — Christopher A. Rothe; CM Law

(57) ABSTRACT

An infusion arrangement for administering a medical fluid includes a medical elastomer pump that produces a delivery pressure dependent on expansion and thus is variable over an infusion duration, a fluid conduit path provided for discharging the medical fluid from the elastomer pump, and a fluid control device arranged in the fluid conduit path and designed to influence a volumetric flow of the medical fluid delivered through the fluid conduit path by the elastomer pump. The fluid control device has a hydraulic flow-regulating valve designed to regulate the volumetric flow to a setpoint value and is provided with a throttle action that is (Continued)

Figure 1:
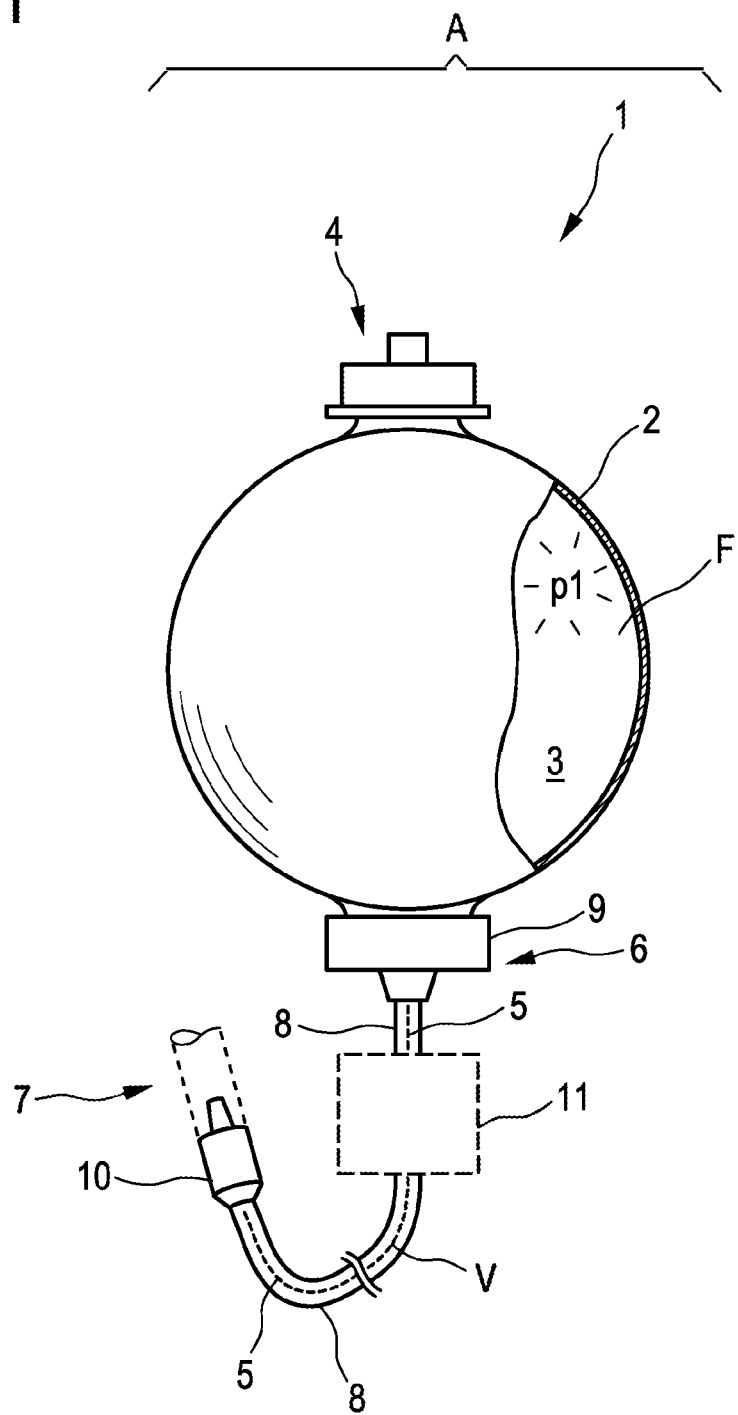

automatically variable at least in accordance with the delivery pressure. The infusion arrangement can be used in infusion therapy.

7 Claims, 4 Drawing Sheets

(52) U.S. Cl.
CPC ............... *A61M 2205/3334* (2013.01); *A61M 2205/3341* (2013.01)

(58) Field of Classification Search
CPC ............ A61M 5/1486; A61M 5/14586; A61M 5/14593; A61M 5/16881; A61M 5/16887; A61M 2205/3334; A61M 2205/3128; A61M 39/22; A61M 39/228; A61M 39/24; A61M 2039/242; A61M 2005/14513; F16K 11/00; F16K 7/00; F16K 7/02; F16K 7/04; F16K 7/045; F16K 7/06; F16K 7/16; F16K 31/1264; F61K 31/1262; F61K 31/1264
See application file for complete search history.

(56) References Cited

U.S. PATENT DOCUMENTS

| | | | | |
|---|---|---|---|---|
| 3,874,629 | A * | 4/1975 | Fontaine | F16K 31/365 251/61.4 |
| 8,028,712 | B2 * | 10/2011 | Grenaway | F16K 31/1264 137/116.5 |
| 2004/0168723 | A1 | 9/2004 | Black | |
| 2004/0171987 | A1 | 9/2004 | Bridle et al. | |
| 2013/0053823 | A1 * | 2/2013 | Fiering | A61M 31/002 604/246 |
| 2018/0200475 | A1 * | 7/2018 | Allum | A61M 16/20 |
| 2019/0105057 | A1 * | 4/2019 | Radl | A61B 17/12109 |

FOREIGN PATENT DOCUMENTS

| | | | | |
|---|---|---|---|---|
| DE | 2337947 | A1 | 2/1975 | |
| EP | 1321156 | A1 * | 6/2003 | ........ A61M 5/16881 |

OTHER PUBLICATIONS

Written Opinion received in International Application No. PCT/EP2019/079107 dated Feb. 12, 2020, with translation, 14 pages.

* cited by examiner

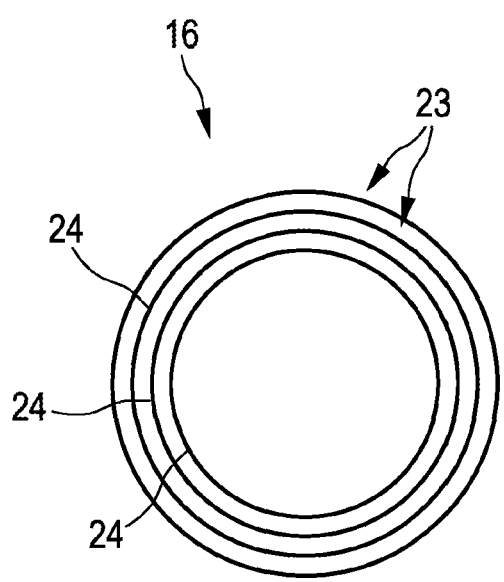

INFUSION ARRANGEMENT FOR ADMINISTERING A MEDICAL FLUID

CROSS-REFERENCE TO RELATED APPLICATION(S)

This application is the United States national phase entry of International Application No. PCT/EP2019/079107, filed Oct. 24, 2019, and claims the benefit of priority of German Application No. 10 2018 220 890.5, filed Dec. 4, 2018. The contents of International Application No. PCT/EP2019/079107 and German Application No. 10 2018 220 890.5 are incorporated by reference herein in their entireties.

FIELD

The invention relates to an infusion arrangement for administering a medical fluid, having a medical elastomer pump with an elastomer membrane which forms a pump volume for receiving and delivering the medical fluid, wherein the elastomer membrane, in a filling state of the pump volume at least partially filled with the medical fluid, has an elastic expansion dependent on the filling state, and wherein the elastic expansion subjects the pump volume to a delivery pressure that is dependent on expansion and thus variable over an infusion duration, a fluid conduit path which is provided for discharging the medical fluid from the pump volume and which at one end is fluidically connected to an outlet of the pump volume and at the other end is fluidically connectable to a patient port, and a fluid control device which is arranged in the fluid conduit path and is designed to influence a volumetric flow of the medical fluid delivered through the fluid conduit path by means of the elastomer pump.

BACKGROUND

An infusion arrangement of this kind is generally known in medicine and is provided for administering a medical fluid in the context of an infusion therapy. The known infusion arrangement has a medical elastomer pump with an elastomer membrane. Such medical elastomer pumps are well known in the medical field and can also be designated as elastomer infusion pumps. The elastomer membrane forms a pump volume which serves to receive and deliver the medical fluid. Depending on the filling state of the pump volume, the elastomer membrane is expanded to a greater or lesser extent in the manner of a balloon and subjects the pump volume to a delivery pressure that is dependent on the filling state and thus variable over an infusion duration. To discharge the medical fluid from the pump volume, the known infusion arrangement has a fluid conduit path. The latter is at one end fluidically connected to an outlet of the pump volume. At the other end, the fluid conduit path is fluidically connectable to a patient port. Moreover, the known infusion arrangement has a fluid control device which is arranged in a fluid-guiding manner in the fluid conduit path. The fluid control device serves to influence the volumetric flow of the medical fluid delivered through the fluid conduit path by means of the elastomer pump. In the known infusion arrangement, the fluid control device is designed in the form of a flow rate limiter, which can also be designated as a flow throttle, and is designed to limit the volumetric flow to a predetermined nominal value.

SUMMARY

The object of the invention is to make available an infusion arrangement which is of the aforementioned type and which permits improved administration of the medical fluid.

This object is achieved by the fact that the fluid control device has a hydraulic flow-regulating valve, which is designed to regulate the volumetric flow to a setpoint value and is provided with a throttle action that is automatically variable at least in accordance with the delivery pressure. The invention proceeds from the consideration that, for design reasons, the delivery pressure of the elastomer pump drops as the filling state of the pump volume decreases. Moreover, in the practical use of the infusion arrangement, the delivery pressure is influenced by further external factors. Such factors are in particular a temperature of the medical fluid to be administered, an ambient temperature, an external pressure on the pump volume, a height difference between the pump volume and the patient port, the nature of a patient port (central or peripheral), etc. By virtue of the solution according to the invention, it is possible to counteract an influence of the delivery pressure, variable for the abovementioned design reasons and/or on account of external factors, on the volumetric flow and thereby permit regulated dispensing of the medical fluid. In particular, by means of the volumetric flow being regulated according to the invention to the setpoint value, it is possible to achieve a dispensing of the medical fluid that is constant, at least averaged over time. Accordingly, inadvertent underdosing or overdosing of the medical fluid is avoided, and an improved administration of the medical fluid is thus permitted. For this purpose, the fluid control device has the hydraulic flow-regulating valve. The flow-regulating valve is designed to regulate the volumetric flow to a setpoint value and is for this purpose provided with a throttle action that is automatically variable at least in accordance with the delivery pressure. In the event of a decreasing delivery pressure, the throttle action can be automatically reduced and thus the volumetric flow can be increased in the direction of the setpoint value. In the event of a delivery pressure being increased for example by said external factors, the throttle action can be automatically increased and thus the volumetric flow can be reduced in the direction of the setpoint value. The basic design and basic function of hydraulic flow-regulating valves are generally known as such in the field of fluid technology. In this respect, the flow-regulating valve can be designed in particular as a 2-way or 3-way flow-regulating valve, a differential pressure volumetric flow regulator or the like. The medical elastomer pump is preferably designed in such a way that it is possible to do without an external energy supply for generating the delivery pressure and/or other functions of the medical elastomer pump. Accordingly, the flow-regulating valve is preferably designed in such a way that it is possible to do without an external energy supply for regulating the volumetric flow. The fluid conduit path can in particular be formed by a fluid conduit duct, a hose line, a tube line or the like. The fluid control device thus forms a section of the fluid conduit path and, during the operation of the medical elastomer pump, is arranged in the volumetric flow of the medical fluid. The fluid control device can be designed and/or arranged separately from the medical elastomer pump and in particular can be arranged fluidically between two sections of the fluid conduit path downstream from the pump volume. Alternatively, the fluid control device can be structurally integrated in the elastomer pump.

In one embodiment of the invention, the flow-regulating valve has a constant control characteristic, wherein the throttle action is automatically constantly variable, or the flow-regulating valve has a non-constant 2-point control characteristic, wherein the throttle action is automatically alternately variable between a blocking and an enabling of the volumetric flow. Regulators with a constant and regulators with a non-constant 2-point control characteristic are as such generally known in the field of control engineering. The first variant mentioned, with a constant control characteristic, has proven advantageous in particular for infusion arrangements for administering a continuous basal rate of the medical fluid. The second variant mentioned, with a non-constant control characteristic, is advantageous in particular for infusion arrangements that serve for a bolus administration of the medical fluid. The throttle action of the flow-regulating valve here changes automatically between a shut-off blocking state and an enabled enabling state. In the blocking state of the flow-regulating valve, there is no volumetric flow. By contrast, in the enabling state, the volumetric flow is enabled. It has also been shown that the non-constant 2-point control characteristic can counteract undesired blockage of the infusion arrangement. Specifically, as a result of the automatic and alternating change of the throttle action between blocking and enabling of the volumetric flow, an undesired adherence of particles in the fluid conduit path and thus blockage of the latter is counteracted.

In a further embodiment of the invention, the hydraulic flow-regulating valve is a 2-way flow-regulating valve and has a first flow resistor, on which the delivery pressure acts at the inlet side and an outlet pressure acts at the outlet side, and a second flow resistor, which has the automatically variable throttle action and is located downstream from the first flow resistor in the delivery direction of the volumetric flow, and a pressure scale arrangement with a hydraulically movable actuating element which is subjected at one end to the delivery pressure and at the other end to the outlet pressure and by means of which the second flow resistor is automatically variable in accordance with a movement of the actuating element caused by differential pressure. In the field of fluid technology, 2-way flow-regulating valves as such are generally known. In the present case, the 2-way flow-regulating valve has a first flow resistor, which can also be designated as a measuring throttle or measuring diaphragm. At the first flow resistor, there is a pressure drop which results from the delivery pressure at the inlet side and the outlet pressure at the outlet side. The pressure drop can also be designated as differential pressure or pressure difference. The outlet pressure is the hydraulic pressure present at the patient-side end of the fluid conduit path. The second flow resistor is arranged downstream from the first flow resistor and is automatically variable in terms of its throttle action by means of the actuating element of the pressure scale arrangement. The actuating element of the pressure scale arrangement is subjected at one end to the delivery pressure and at the other end to the outlet pressure, and it is movable under the effect of differential pressure in order to change the throttle action of the second flow resistor. The embodiment of the hydraulic flow-regulating valve as a 2-way flow-regulating valve is particularly advantageous, especially as regards the reliability and robustness of the regulation of the volumetric flow.

In a further embodiment of the invention, the first flow resistor is a capillary element which locally narrows the fluid conduit path and which causes a pressure difference, which is small compared to the delivery pressure, between delivery pressure and outlet pressure, wherein the pressure difference is preferably smaller than the delivery pressure by a factor of 10 to 20, preferably 20 to 100, particularly preferably 100 to 1000. Accordingly, the first flow resistor has a comparatively low hydraulic resistance. In this way, it is possible in particular to counteract an unwanted blockage of the fluid conduit path. The capillary element can be designed in particular as a small tube, a locally narrowed hose portion or a tube portion. The hydraulic resistance of the capillary element is preferably non-adjustable.

In a further embodiment of the invention, the capillary element has a flow-effective cross section which measures at least 100 µm, preferably 100 µm to 150 µm. By means of this embodiment of the invention, it is possible, in a particularly simple way, to counteract a blockage of the fluid conduit path in the region of the capillary element. It has been found that an effective cross section of 100 µm to 150 µm is particularly advantageous in the use of medical fluids, as are used in particular in chemotherapy or antibiotic therapy.

In a further embodiment of the invention, the pressure scale arrangement has a spring element, which is operatively connected to the actuating element and subjects the actuating element to a spring force. The spring element serves for restoring or pretensioning the actuating element by a spring force. By means of the spring element, it is possible to achieve an improved state of equilibrium of the actuating element in the control operation and thus an improved operating behavior of the 2-way flow-regulating valve.

In a further embodiment of the invention, an adjustment device is provided, by means of which the spring force of the spring element is manually adjustable. The adjustment device thus serves directly for setting an equilibrium state of the actuating element and thus for setting a setpoint pressure difference between delivery pressure and outlet pressure. This embodiment of the invention is particularly advantageous if the first flow resistor is designed as a non-adjustable flow resistor. In this case, a setting of the setpoint pressure difference and therefore of the setpoint value of the volumetric flow can be achieved by means of the adjustment device. This is because the volumetric flow is proportional to the pressure difference in accordance with the physical interrelationships that are of relevance here.

In a further embodiment of the invention, the actuating element is designed in the form of a pressure piston or in the form of a pressure membrane. By designing the actuating element in the form of a pressure piston, it is possible to obtain a particularly robust and easy-to-produce embodiment of the 2-way flow-regulating valve. The second variant, in which the actuating element is designed in the form of a pressure membrane, is particularly non-sensitive to contamination and to any adhering or sticking of the actuating element caused by the medical fluid that is delivered.

In a further embodiment of the invention, the pressure membrane has a bead arrangement extending about the periphery in the manner of a loudspeaker diaphragm. The bead arrangement has the effect that the pressure membrane itself has only a very slight restoring force in relation to a movement caused by differential pressure. In this way, the pressure membrane is reliably movable, even in the case of very slight pressure differences between delivery pressure and outlet pressure.

BRIEF DESCRIPTION OF THE DRAWING FIGURES

Further advantages and features of the invention will become clear from the following description of preferred exemplary embodiments of the invention, which are illustrated by way of the drawings.

Figure 2:
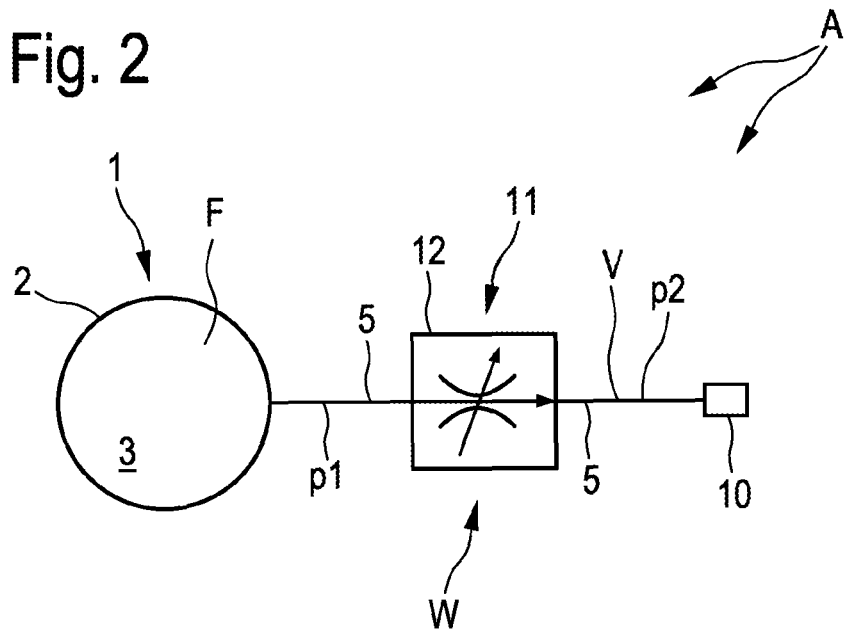
Figure 3:
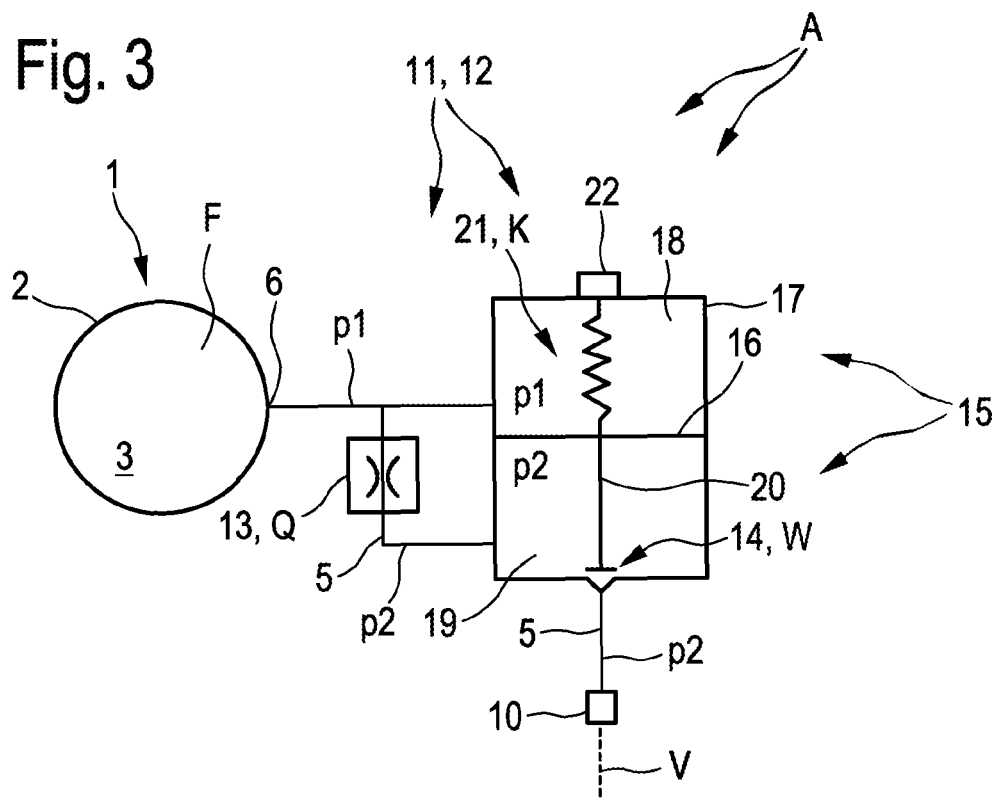
Figure 4:
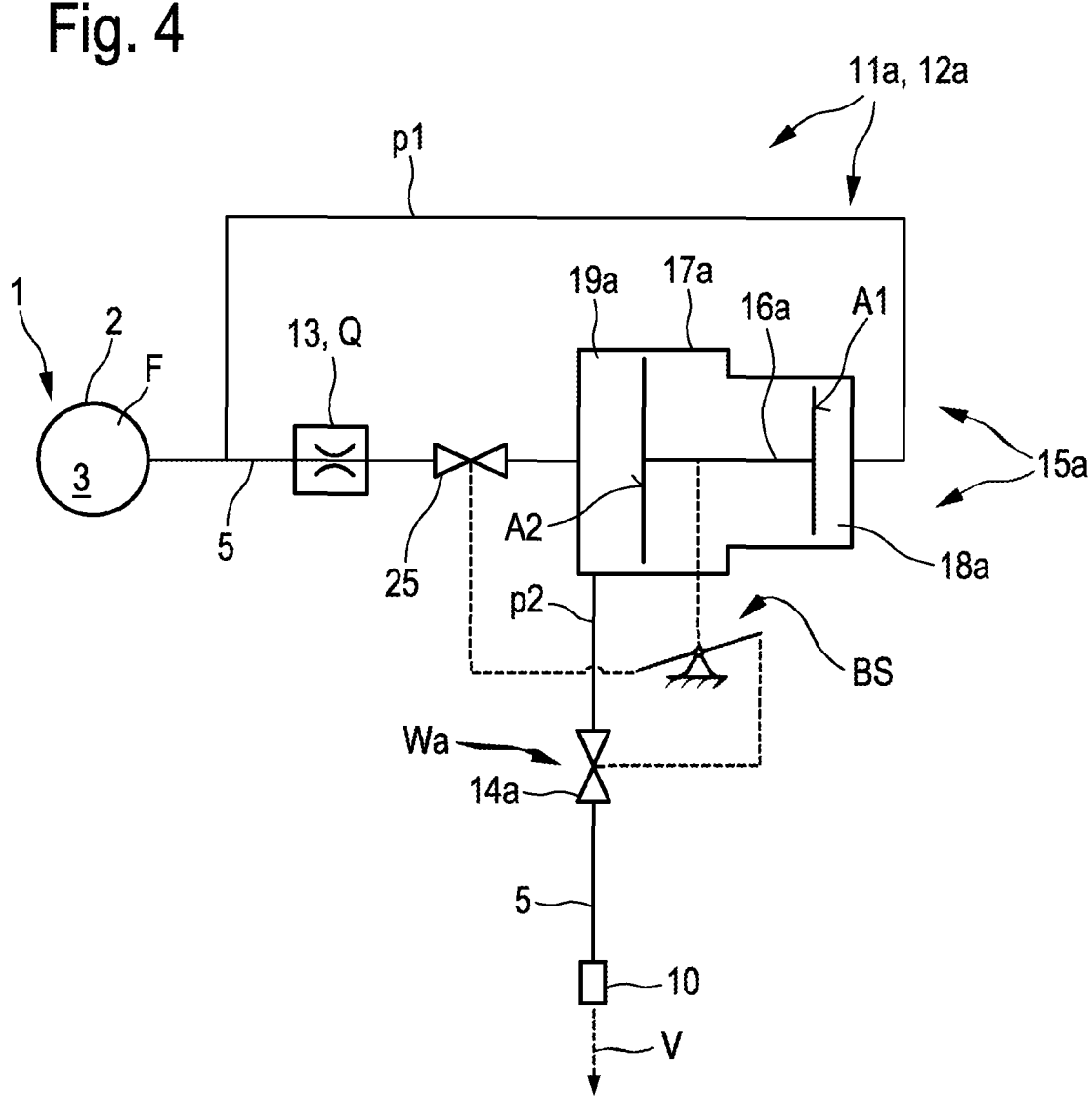

FIG. 1 shows a schematic and partially sectioned view of an embodiment of an infusion arrangement according to the invention, with a symbolically illustrated fluid control device, FIG. 2 shows the infusion arrangement according to FIG. 1 in a greatly simplified schematic view in the manner of a hydraulic circuit diagram, FIG. 3 shows the infusion arrangement according to FIGS. 1 and 2 in a further schematic view, which illustrates details of the fluid control device, FIG. 4 shows, in a schematic view corresponding to FIG. 3, a further embodiment of an infusion arrangement according to the invention, and FIG. 5 shows a schematic detail of a pressure membrane of the infusion arrangement according to FIGS. 1 to 3.

DETAILED DESCRIPTION

According to FIG. 1, an infusion arrangement A is provided for administering a medical fluid F in the context of outpatient and/or inpatient infusion therapy. The infusion arrangement A has a medical elastomer pump 1, which can also be referred to as an elastomer infusion pump. The medical elastomer pump 1 has an elastomer membrane 2 which forms a pump volume 3 for receiving and delivering the medical fluid F. In the configuration shown in FIG. 1, the pump volume 3 is shown in a filling state in which it is filled with the medical fluid F. In this filling state, the elastomer membrane 2 has an elastic expansion dependent on the filling state and is flexibly expanded like a balloon. The elastic expansion of the membrane 2 subjects the pump volume 3 to a delivery pressure p1 that is variable depending on the expansion and thus implicitly depending on the filling state. With reference to FIG. 1, the membrane 2 is illustrated with an exaggerated wall thickness for graphic reasons. For the purpose of filling the pump volume 3 with the medical fluid F, the elastomer pump 1 has a reclosable filling nozzle 4, which is joined to the membrane 2 in a fluid-tight manner that is known in principle.

To discharge the medical fluid F from the pump volume 3, the infusion arrangement A has a fluid conduit path 5 which at one end is fluidically connected to an outlet 6 of the pump volume 3 and at the other end is fluidically connectable to a patient port 7. In the present case, the fluid conduit path 5 is formed by means of a flexible hose line 8 which can be arranged in one piece or as a plurality of subportions that are fluidically interconnected. At its end directed toward the outlet 6, the hose line 8 is connected firmly and fluid-tight to an outlet nozzle 9 of the elastomer pump 1 assigned to the outlet 6, the connection being made in a manner that is known in principle. The outlet nozzle 9 forms a fluid-guiding transfer from the pump volume 3 through the outlet 6 into the fluid conduit path 5. At its end directed toward the patient port 7, the hose line 8 has an attachment element 10, which in the present case is designed for example in the form of a Luer connector (shown in a greatly simplified schematic form). In one embodiment not shown, the attachment element 10 can be designed in the form of an attachment marketed under the trademark NRFit™. The Luer connector 10 is provided for fluidic connection to the patient port 7. The patient port 7 is shown only in a highly simplified and partially sectioned schematic view in FIG. 1.

The infusion arrangement A moreover has a fluid control device 11 arranged in the fluid conduit path 5. The fluid control device 11 is designed to influence a volumetric flow V of the medical fluid F delivered through the fluid conduit path 5 by means of the elastomer pump 1. In this respect, the fluid control device 11 is fluidically connected in a fluid-guiding manner at one end to an upper segment (upper with respect to the drawing plane of FIG. 1) of the hose line 8 and is fluidically connected at the other end to a lower segment of the hose line 8, neither segment being shown in detail. The fluid conduit path 5 thus extends at least in part through the fluid control device 11.

The infusion arrangement A is in the present case dimensioned in such a way that it can be readily worn on the body by a patient. The elastomer pump 1 and the fluid control device 11 are in this case both designed in such a way that they are each able to be operated without an external energy supply. Accordingly, there is no need for any electrical supply lines or electrical energy storage units for supplying the elastomer pump 1 and/or the fluid control device 11 with electrical operating energy. The elastomer pump 1 is accordingly light and dimensionally compact, wherein in the present case the pump volume 3 has a nominal size of 400 ml. It goes without saying that the pump volume 3 may also have a different size, for example of 50 ml to 1000 ml.

As will also be seen from FIG. 2, the fluid control device 11 has a hydraulic flow-regulating valve 12. The flow-regulating valve 12 is designed to regulate the volumetric flow V to a setpoint value (not defined in detail) and is provided with a throttle action W that is automatically variable at least in accordance with the delivery pressure p1. The automatically variable throttle action W thus produces a pressure drop $\Delta p$, automatically variable by means of the flow-regulating valve 12, between an inlet and an outlet of the fluid control device 11. This pressure drop $\Delta p$ can also be designated as pressure difference $\Delta p$ or differential pressure $\Delta p$ and is composed of the delivery pressure p1 at the inlet and of an outlet pressure p2 at the outlet of the fluid control device 11 and thus at the attachment element 10. On the simplified assumption of a purely laminar stationary flow and a homogeneous Newtonian fluid, the volumetric flow V in the present case can be described on the basis of the Hagen-Poiseuille law. Accordingly, the volumetric flow V is proportional to the differential pressure $\Delta p$.

Over the duration of the infusion therapy, which can also be designated as the infusion duration, the filling state of the pump volume 3 decreases on account of the medical fluid F being discharged from same. As a result of this decrease of the filling state, the elastic expansion of the membrane 2 reduces, and thus of course also the expansion-dependent delivery pressure p1. Without controlling intervention, this filling-state-dependent decrease of the delivery pressure p1 would necessarily lead to an undesired decrease in the volumetric flow V. In order to compensate for this, the throttle action W is variable in accordance with the delivery pressure p1, in a way that is described in more detail below. To be more precise, the throttle action W can be automatically reduced if there is a filling-state-induced decrease in the delivery pressure p1, such that the differential pressure $\Delta p$ between delivery pressure p1 and outlet pressure p2 is regulated to a pressure setpoint value. The volumetric flow V is thus also able to be regulated to said setpoint value. Equally, a corresponding increase in the throttle action W can take place if the delivery pressure p1 increases on account of external factors. Further details of the flow-regulating valve 12 will be seen in particular from FIG. 3.

As can be seen from FIG. 3, the hydraulic flow-regulating valve 12 has a first flow resistor 13, a second flow resistor 14, and a pressure scale arrangement 15 with a hydraulically movable actuating element 16. The hydraulic flow-regulating valve is in this respect designed in the form of a 2-way flow-regulating valve 12.

The first flow resistor 13 is in the present case designed in the form of a capillary element. The capillary element 13 forms a local narrowing of the fluid conduit path 5 and is fluidically connected at the inlet end to the outlet 6 of the elastomer pump 1. At the inlet end, the delivery pressure $p1$ thus acts on the capillary element 13.

The pressure scale arrangement 15 is shown in a highly simplified schematic view and is designed in the form of a membrane pressure scale. The actuating element is in this respect designed in the form of a pressure membrane 16. The pressure membrane 16 is subjected to the delivery pressure $p1$ on an upper membrane side, with respect to the drawing plane of FIG. 3, and is subjected to the outlet pressure $p2$ on a lower membrane side. The pressure membrane 16 is fitted at its edge in a fluid-tight manner into a pressure housing 17, in a manner known in principle. The pressure housing 17 has an upper pressure chamber 18, which is assigned to the upper side of the membrane 16, and a lower pressure chamber 19, which is assigned to the underside of the pressure membrane 16. The pressure membrane 16 is movable in the vertical direction of the pressure housing 17 under the effect of differential pressure, in a manner known in principle, and is provided on the underside with a tappet element 20 which, together with a housing-side outlet opening (not shown in detail), forms the second flow resistor 14. The second flow resistor 14 has the automatically variable throttle action $W$ which, in the present case, is variable on account of differential pressure by means of a movement of the pressure membrane 16. Downstream from the second flow resistor 14, the fluid conduit path 5 opens into the attachment element 10.

A spring element 21 is moreover provided which in the present case is arranged in the upper pressure chamber 18 and produces a spring force $K$ on the pressure membrane 16. The spring force $K$ counteracts a movement of the pressure membrane 16 in the direction of the upper pressure chamber 18. The spring element 21 is in the present case designed in the form of a helical spring which at one end is supported on the pressure housing 17 and at the other end is supported on the pressure membrane 16 at the top.

To explain the function of the fluid control device 11, a stationary state is initially assumed below, in which the upper pressure chamber 18 is subjected to the delivery pressure $p1$ and the lower pressure chamber 19 is subjected to the outlet pressure $p2$. In this respect, the pressure drop $\Delta p$ takes place over the capillary element 13, wherein the volumetric flow $V$ pouring through the outlet element 10 is proportional to the pressure drop or differential pressure $\Delta p$. In this state, the pressure scale arrangement 15 is situated in a force equilibrium in which the spring force $K$ and the delivery pressure $p1$ act on the top of the pressure membrane 16 and only the outlet pressure $p2$ acts on the underside. The pressure membrane 16 in the present case is dimensioned identically at the top side and underside, such that in each case a surface of the same dimensions is subject to pressure. In this state, which can also be designated as the control equilibrium, it follows from a consideration of the force equilibrium on the pressure membrane 16 that the differential pressure $\Delta p$ is equal to the quotient of the spring force $K$ and the pressure-subjected surface of the pressure membrane 16. Thus, on the basis of the above-described law, the differential pressure $\Delta p$, hence the volumetric flow $V$, is independent of the delivery pressure $p1$ and independent of the outlet pressure $p2$.

If the delivery pressure $p1$ now drops on account of the filling state, the pressure membrane 16, starting from the above-described state of equilibrium, moves upward counter to the spring force $K$, as a result of which the second flow resistor 14 is influenced via the tappet element 20. To be more precise, the second flow resistor 14 is reduced here in respect of its throttle effect $W$. In the present case, this takes place, in a manner known in principle, through an increase in an effective cross section of flow of the second flow resistor 14. In this way, the outlet pressure $p2$ drops accordingly, wherein the differential pressure $\Delta p$ is constantly regulated according to the above-described force equilibrium. In this way, the volumetric flow $V$ is in turn regulated to the setpoint value proportional to the differential pressure $\Delta p$. The same applies, conversely, in the event of an undesired temporary increase in the delivery pressure $p1$ as a result of external factors, for example a temperature increase or an external pressure load on the elastomer membrane 2.

In the present case, the capillary element 13 has a non-adjustable flow resistor. However, in order to permit an adjustability of the volumetric flow $V$, an adjustment device 22 is provided here, by means of which the spring force $K$ of the spring element 21 is manually adjustable. The adjustment device 22 is arranged at the top side of the pressure housing 17 and is designed in such a way that an increased and/or reduced axial pretensioning of the spring element 21 can be set. For this purpose, the adjustment device 21 can be screwed for example with a thread into the pressure housing 17, which converts a rotary manual adjustment movement of the adjustment device 22 into an axial pretensioning movement for influencing the spring force $K$. As has been set out above, the differential pressure $\Delta p$, hence the volumetric flow $V$, is in control equilibrium, i.e. at a force equilibrium of the pressure membrane 16, proportional to the quotient of the spring force $K$ and the pressure surface of the pressure membrane 16. Accordingly, the volumetric flow $V$ can be set easily and effectively in the equilibrium state by manual adjustment of the spring force $K$ by means of the adjustment device 22. The volumetric flow $V$ in the equilibrium state of the flow-regulating valve 11 defines the setpoint value to which the volumetric flow $V$ is to be regulated.

In the present case, the capillary element 13 produces a small pressure drop $\Delta p$ in comparison with the delivery pressure $p1$. Accordingly, a flow-effective cross section $Q$ of the capillary element 13 is of comparatively large dimension. In the present case, the flow-effective cross section $Q$ of the capillary element 13 measures approximately 150 μm.

Further details of the pressure membrane 16 are illustrated schematically in FIG. 5. It can be seen there that the pressure membrane 16 has a bead arrangement 23 extending about the periphery. The bead arrangement 23 is configured in the manner of a loudspeaker diaphragm and has a plurality of concentric beads 24. Three beads 24 are provided in the present case. The bead arrangement 23 has the effect that the pressure membrane 16 is at least substantially free, preferably virtually completely free, from restoring forces. This permits in particular an improved adjustability of the control equilibrium of the flow-regulating valve 12.

As is clear from the above description of the function of the flow-regulating valve 12, the flow-regulating valve 12 in the embodiment shown in FIG. 3 has a constant control characteristic. This means that the throttle action $W$ is automatically constantly variable, i.e. continuously between a large number of different values.

By contrast, the flow-regulating valve 12a seen in FIG. 4 has a non-constant 2-point control characteristic, wherein the throttle action Wa is automatically alternately variable between a blocking and an enabling of the volumetric flow V. Only the essential differences between the embodiment shown in FIG. 4 and the embodiment shown in FIG. 3 are discussed below. Structurally identical elements and sections are provided here with identical reference signs. Features that have a different structural and/or functional configuration compared to the embodiment according to FIG. 3 are identified by addition of the lowercase letter a. Otherwise, in order to avoid repetition, reference is made to the disclosure in connection with FIGS. 1 to 3, which disclosure correspondingly applies for the embodiment according to FIG. 4.

The embodiment according to FIG. 4 differs from the embodiment according to FIG. 3 essentially in terms of the different configuration of the pressure scale arrangement 15a and the associated non-constant 2-point control characteristic. The pressure scale arrangement 15a has a hydraulically movable actuating element in the form of a pressure piston 16a. The pressure piston 16a is guided in a hydraulically movable manner in a pressure housing 17a and in the present case has different piston surfaces subjected to pressure. A first piston surface A1 is arranged in a first pressure chamber 18a of the pressure housing 17a. A second piston surface A2 is arranged in a second pressure chamber 19a of the pressure housing 17a. The first piston surface A1 is subjected to the delivery pressure p1. The second piston surface A2 is subjected to the outlet pressure p2.

Moreover, in contrast to the embodiment according to FIG. 3, the second flow resistor is configured in the form of a shut-off valve 14a. The shut-off valve 14a is arranged in the fluid conduit path 5 downstream from the second pressure chamber 19a and is movable between a blocking position and an enabling position by means of a schematically indicated bistable toggle switch BS. In the blocking position, the volumetric flow V is shut off by means of the shut-off valve 14a. In the enabling position, by contrast, the volumetric flow V is enabled. The bistable toggle switch BS can be actuated in accordance with a differential-pressure-induced movement of the pressure piston 16a, as is illustrated by the operative connection (indicated by a broken line and not in detail) between the bistable toggle switch BS and the pressure piston 16a. The first flow resistor 13 corresponds to the first flow resistor 13 of the infusion arrangement A according to FIG. 3. Moreover, a further shut-off valve 25 is provided which, with respect to the intended delivery direction of the medical fluid F, is arranged downstream from the first flow resistor 13 and upstream from the second pressure chamber 19a. The second shut-off valve 25 is likewise movable between a blocking position and an enabling position by means of the bistable toggle switch BS. This is illustrated by means of the operative connection (indicated by a broken line) between the toggle switch BS and the second shut-off valve 25. In this embodiment of the invention, the differential pressure $\Delta p$ between delivery pressure p1 and outlet pressure p2 is defined by the size ratios of the first piston surface A1 and the second piston surface A2.

By means of the differential-pressure-induced hydraulic movement of the pressure piston 16a, the shut-off valve 14a and the second shut-off valve 25 can be switched alternately by means of the toggle switch BS such that the first shut-off valve 14a is always blocked when the second shut-off valve 25 is enabled, and vice versa.

In a first state, the second shut-off valve 25 is enabled and the first shut-off valve 14a is blocked. On account of the different size ratios of the piston surfaces A1, A2, the pressure piston 16a moves to the right, with respect to the drawing plane of FIG. 4. Here, the second pressure chamber 19a is filled to an increased extent, while the first pressure chamber 18a by contrast is emptied.

Starting from a predetermined position of the pressure piston 16a, the bistable toggle switch BS is actuated via the operative connection to the pressure piston 16a, wherein the second shut-off valve 25 is blocked and the first shut-off valve 14a is enabled. In this second state, the delivery pressure p1 acting on the piston surface A1 produces a movement of the pressure piston 16a to the left, such that the second pressure chamber 19a is emptied via the fluid conduit path 5 in the direction of the attachment element 10. This results in the volumetric flow V. Starting from a certain limit position, the bistable toggle switch BS is once again actuated by means of the pressure piston 16a, as a result of which the switching state of the shut-off valves 14a, 25 is alternately changed. Thereafter, the above-described cycle is run through again. The above-described 2-point control characteristic of the flow-regulating valve 12a is particularly advantageous in relation to a bolus-like administration of the medical fluid F averaged over time and regulated by the volumetric flow.

The invention claimed is:
1. An infusion arrangement for administering a medical fluid, comprising:
  a medical elastomer pump with an elastomer membrane which forms a pump volume for receiving and delivering the medical fluid, wherein the elastomer membrane, in a filling state of the pump volume at least partially filled with the medical fluid, has an elastic expansion dependent on the filling state, and wherein the elastic expansion subjects the pump volume to a delivery pressure that is dependent on expansion and thus variable over an infusion duration,
  a fluid conduit path which is provided for discharging the medical fluid from the pump volume and which at a first end is fluidically connected to an outlet of the pump volume and at a second end is fluidically connectable to a patient port, and
  a fluid control device which is arranged in the fluid conduit path and is designed to influence a volumetric flow of the medical fluid delivered through the fluid conduit path by the medical elastomer pump,
  wherein the fluid control device has a hydraulic flow-regulating valve, which is designed to regulate the volumetric flow to a setpoint value and is provided with a throttle action that is automatically variable at least in accordance with the delivery pressure, and
  wherein the hydraulic flow-regulating valve is a 2-way hydraulic flow-regulating valve and has a first flow resistor, on which the delivery pressure acts at an inlet side and an outlet pressure acts at an outlet side, and a second flow resistor, which has the throttle action and is located downstream from the first flow resistor in a delivery direction of the volumetric flow, and a pressure scale arrangement with a hydraulically movable actuating element which is subjected at one end to the delivery pressure and at another end to the outlet pressure and by which the second flow resistor is automatically variable in accordance with a movement of the hydraulically movable actuating element caused by differential pressure.

2. The infusion arrangement as claimed in claim 1, wherein the hydraulic flow-regulating valve has a constant control characteristic, wherein the throttle action is automatically constantly variable, or the hydraulic flow-regulating valve has a non-constant 2-point control characteristic, wherein the throttle action is automatically alternately variable between a blocking and an enabling of the volumetric flow.

3. The infusion arrangement of claim 1, wherein the hydraulically movable actuating element comprises a pressure piston or a pressure membrane.

4. The infusion arrangement of claim 1, wherein the first flow resistor is a capillary element which locally narrows the fluid conduit path and which produces a pressure difference, which is small compared to the delivery pressure, between the delivery pressure and the outlet pressure, wherein the pressure difference is smaller than the delivery pressure by a factor of 10 to 20.

5. The infusion arrangement of claim 4, wherein the capillary element has a flow-effective cross section which measures at least 100 μm.

6. The infusion arrangement of claim 1, wherein the pressure scale arrangement has a spring element, which is operatively connected to the hydraulically movable actuating element and subjects the hydraulically movable actuating element to a spring force.

7. The infusion arrangement of claim 6, wherein an adjustment device is provided, by which the spring force of the spring element is manually adjustable.

\* \* \* \* \*